(12) United States Patent
Lovick

(10) Patent No.: US 11,570,981 B2
(45) Date of Patent: Feb. 7, 2023

(54) HYDRATION MEDIA FOR BIOLOGICAL TISSUE PRODUCTS, METHODS OF MAKING THE SAME AND METHODS OF USING

(71) Applicant: Bacterin International, Inc., Belgrade, MT (US)

(72) Inventor: Helena M. Lovick, N. Great Falls, MT (US)

(73) Assignee: Bacterin International, Inc., Belgrade, MT (US)

( * ) Notice: Subject to any disclaimer, the term of this patent is extended or adjusted under 35 U.S.C. 154(b) by 796 days.

(21) Appl. No.: 16/460,990

(22) Filed: Jul. 2, 2019

(65) Prior Publication Data
US 2020/0000086 A1 Jan. 2, 2020

Related U.S. Application Data

(60) Provisional application No. 62/693,275, filed on Jul. 2, 2018.

(51) Int. Cl.
*A01N 1/02* (2006.01)
*A61L 27/36* (2006.01)

(52) U.S. Cl.
CPC .......... *A01N 1/021* (2013.01); *A01N 1/0263* (2013.01); *A61L 27/3683* (2013.01)

(58) Field of Classification Search
None
See application file for complete search history.

(56) References Cited

U.S. PATENT DOCUMENTS

| 6,293,970 | B1 | 9/2001 | Wolfinbarger, Jr. et al. |
| 6,569,200 | B2 | 5/2003 | Wolfinbarger, Jr. et al. |
| 6,739,112 | B1 | 5/2004 | Marino |
| 7,162,850 | B2 | 1/2007 | Marino et al. |
| 8,574,825 | B2 | 11/2013 | Shelby et al. |
| 2019/0045776 | A1* | 2/2019 | Thatte .................. A01N 1/0226 |

FOREIGN PATENT DOCUMENTS

WO WO 2021/050566 * 3/2021

* cited by examiner

*Primary Examiner* — Ralph J Gitomer
(74) *Attorney, Agent, or Firm* — Sheridan Ross P.C.

(57) ABSTRACT

A hydration media for biological tissue products, methods of making the same and methods of using the same is provided. The hydration media includes sodium phosphate and calcium silicate and can be used to store or hydrate a biological tissue product.

18 Claims, 1 Drawing Sheet

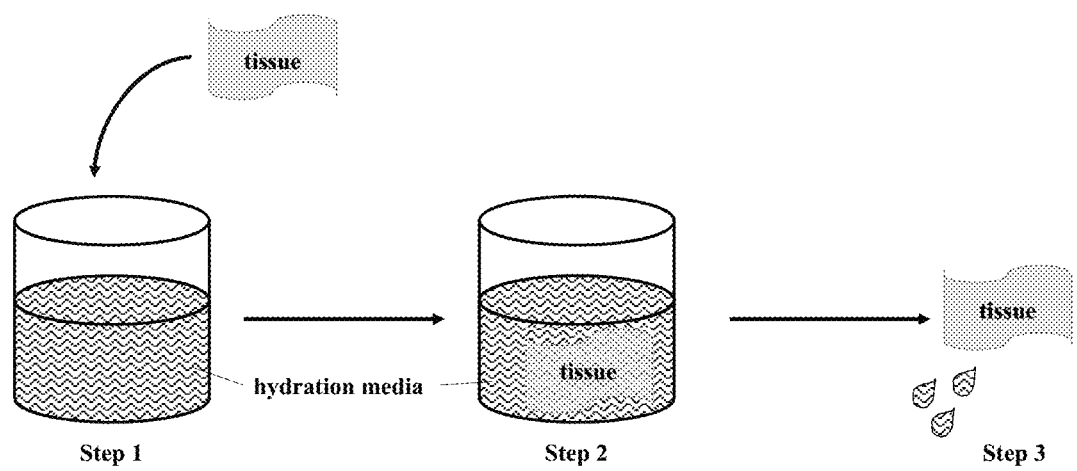

HYDRATION MEDIA FOR BIOLOGICAL TISSUE PRODUCTS, METHODS OF MAKING THE SAME AND METHODS OF USING

CROSS REFERENCE TO RELATED APPLICATION

This application claims priority and the benefit under 35 U.S.C. § 119(e) to U.S. Provisional Patent Application Ser. No. 62/693,275 filed on Jul. 2, 2018, which is incorporated herein in its entirety by reference.

FIELD OF THE INVENTION

The present invention generally relates to a liquid, hydration media for use with biological tissues, apparatuses containing the liquid, hydration media, methods of making the media, and methods of use thereof.

DESCRIPTION OF THE PRIOR ART

Methods for storing hydrated, biological tissue products are known in the prior art. The typical approach to providing a hydrated biological tissue product is storage in saline or buffered saline fluid throughout the product's shelf-life. Alternatively, dried biological tissues may be reconstituted in hydration media to provide a hydrated product prior to use. Routinely, low temperature storage of hydrated biological tissue products is utilized throughout the entirety of the storage period to preserve intrinsic tissue properties. Despite the use of isotonic and physiological pH fluids, the biological tissue products contained in the storage media inevitably demonstrate adverse aging phenomena.

U.S. Pat. No. 7,162,850 to Marino et al. (incorporated in its entirety by reference) discloses a method to package bone allograft during at least one of storage and transportation of the allograft without refrigeration prior to use. The method includes sealing a previously dimensioned bone allograft for use in spinal fusion surgery in a sealed container with a volume of saline solution.

U.S. Pat. No. 6,739,112 to Marino et al. (incorporated in its entirety by reference) discloses a method of providing a bone allograft for use in spinal fusion surgery by sealing a previously dimensioned bone allograft in a sealed container having a volume of saline solution.

The saline solution is provided in an amount sufficient to maintain the bone allograft in a substantially submerged state.

U.S. Pat. No. 6,293,970 to Wolfinbarger, Jr. et al. (Wolfinbarger I) (incorporated by reference in its entirety) discloses a plasticized, load-bearing, bone graft, comprising a cleaned, non-demineralized, load-bearing, bone graft impregnated with one or more plasticizers. In some instances, the plasticizers are suitable for direct transplantation into a human without rehydration of said bone graft.

U.S. Pat. No. 6,569,200 to Wolfinbarger, Jr. et al. (Wolfinbarger II) (incorporated by reference in its entirety) discloses a plasticized bone or soft tissue product that exhibits properties that approximate those material properties of normal hydrated tissue. Methods of producing the plasticized grafts include impregnating the graft with one or more plasticizers by incubating the graft with a plasticizer composition. The plasticizer composition includes one or more plasticizers and one or more biocompatible solvents. In some instances, the plasticizer is glycerol and the biocompatible solvent is isopropyl alcohol.

SUMMARY OF THE INVENTION

A need remains for a storage solution capable of providing biological tissue products in a hydrated state while preserving the inherent characteristics and properties of the tissue. The present invention discloses products and methods that are advantageous over this art.

The invention is directed to a liquid hydration media for biological tissues and a method of manufacturing thereof. The hydration media includes an aqueous solution containing specific concentrations of dissolved ions to maintain and preserve biological tissue products. The dissolved ions and physiological pH range within the hydration media act to prevent mineral leaching from biological tissues. At least one physical property is retained in the biological tissue. The retained physical properties of the biological tissue products include retained elasticity, compressive strength, and shear strength. The method of manufacturing the liquid hydration media relies on a select combination of solutes to provide an isotonic solution and to preserve the biological tissue products. In some embodiments, the hydration medium can be used to rehydrate dried, dehydrated, or lyophilized biological tissue products. In some embodiments, the hydration medium can be used to store biological tissues. In some embodiments, the biological tissues can be stored at temperatures of about −135° C. to about 60° C., about −90° C. to 50° C., or about 0° C. to 30° C. In some embodiments, the biological tissues can be stored at −135° C., −120° C., −100° C., −90° C., −75° C., −50° C., −25° C., −4° C., 0° C., 4° C., 10° C., 15° C., 20° C., 25° C., 30° C., 35° C., 40° C., 45° C., 50° C., 55° C., or 60° C.

At least one biological tissue can be stored or rehydrated with the liquid hydration media. Suitable biological tissues include bone, connective tissue, tendon, pericardium, dermis, cornea, dura mater, fascia, heart valve, ligament, capsular graft, cartilage, collagen, nerve, placental tissue, and combinations thereof. In some embodiments, the biological tissue can be cortical bone, cancellous bone, or combinations thereof. In some embodiments, the bone can be fully demineralized, partially demineralized, mineralized or any combinations thereof. The biological tissues can be partially dehydrated, fully dehydrated, or fully hydrated. The biological tissues can be allogeneic, autogeneic, and xenogeneic tissues, and combinations thereof. In some embodiments, the hydration media can preserve physical properties and the inherent growth factors within the biological tissues.

BRIEF DESCRIPTION OF THE FIGURES

FIG. 1 illustrates a perspective graphical view of the method of use of the hydration media with biological tissue in accordance with the present invention.

DETAILED DESCRIPTION OF THE INVENTION

The present invention relates to a hydration media for use with biological tissue products, an apparatus containing the hydration media and the biological tissue, and methods of using the same.

"Allogeneic" or "allograft", as used herein, refers to tissue derived from a non-identical donor of the same species.

"Autogeneic" or "autograft", as used herein, refers to tissue derived from and implanted into the same identical patient.

"Biocompatible", as used herein, refers to the property of being biologically compatible with a living being by not causing harm.

"Patient", as used herein, refers to a living recipient of the biological tissue products in contact with the hydration media of the present invention.

"Xenogeneic" or "xenograft", as used herein, is defined as tissue derived from a non-identical donor of a different species.

The hydration media for biological tissues of the invention has many advantages over the prior art. The hydration media includes a solution of a phosphate source and calcium silicate in water. The phosphate source can be sodium phosphate, which can be in the form of sodium phosphate dibasic, sodium phosphate monobasic, and combinations thereof and can be anhydrous or hydrated. Other suitable phosphate sources can include counterions that can be found within a mammal, for example potassium phosphate, calcium phosphate, or magnesium phosphate. The hydration media can include the components of sodium phosphate and calcium silicate in a total osmolality range of about 200 to about 400 milliosmoles per kilograms (mOsm/kg), in some embodiments about 220 to about 380 mOsm/kg, about 250 to about 350 mOsm/kg, about 270 to about 330 mOsm/kg, or in some embodiments about 290 to about 310 mOsm/kg. The molar ratio of the sodium phosphate to calcium phosphate can be between 150:1 and 250:1, in some embodiments about 180:1, about 190:1, 200:1, about 210:1, about 220:1, about 230:1, about 240:1, or about 250:1. The calcium silicate component can be present at a concentration of about 0.010 to about 0.150 milligrams per milliliter (mg/mL) of the solution, of about 0.025 to about 0.100 mg/mL of the solution, or of about 0.040 to about 0.85 mg/mL of the solution. In some embodiments, the hydration media can contain other solutes such as potassium, chloride, and magnesium, which can be provided so that the ion is provided (e.g. potassium phosphate, magnesium phosphate, etc.). These optional solutes can be provided by altering the amount of the sodium phosphate provided in the mixture, so long as the osmolality range remains between about 200 and about 400 mOsm/kg. In some embodiments, between about 0.005 M and about 0.01 M of the optional solutes can be provided. In some embodiments, the optional can be provided in an amount of about 0.005 M, about 0.006, about 0.007, about 0.008, about 0.009, or about 0.01M. The hydration media can have a pH range of between about 5.0 to about 10.0, between about 6.0 to about 9.0, or between about 7.0 to about 7.7. In some embodiments, the pH can be about 5.0, about 5.5, about 6.0, about 6.5, about 7.0, about 7.5, about 8.0, about 8.5, about 9.0, about 9.5 or about 10. If the pH falls outside of the allowable range or value, the pH can be adjusted by titrating with an aqueous solution, for example sodium hydroxide or phosphoric acid. In some embodiments, the solution can contain at least one additional solvent other than water. Suitable solvents include ethanol, isopropanol, dimethylsulfoxide, or glycerol. The additional solvent can be present an any amount where the sodium phosphate and calcium silicate remain dissolved, and such that the osmolality remains in the range of about 200 to about 400 mOsm/kg. In some embodiments, the additional solvent can be in present in the amount of about 1% to about 25% by total volume, about 5% to about 20%, about 10% to about 18% by total volume, or about 12% to about 15% by total volume. In some embodiments, the additional solvent by total volume can be present in the amount of about 1%, about 5%, about 10%, about 15%, about 20%, or about 25%. The water of the present invention can be any suitable water, including distilled water, tap water, deionized water, or combinations thereof.

The origins of the biological tissues to be placed in contact with the hydration media can be allogeneic, autogeneic, xenogeneic, or combinations thereof. Suitable biological tissue types can include bone, connective tissue, tendon, pericardium, dermis, cornea, dura mater, fascia, heart valve, ligament, capsular graft, cartilage, collagen, nerve, placental tissue, and combinations thereof. In some embodiments, the biological tissue can be bone, which can be cortical bone, cancellous bone, and combinations thereof. The bone can be fully demineralized bone, partially demineralized bone, and mineralized bone, or combinations thereof. Suitable methods for demineralizing the bone U.S. Pat. No. 8,574,825, which is incorporated by reference in its entirety.

In some embodiments, biological tissue can be contacted with the hydration media for about 1 minute to 5 years, about 1 minute to 3 years, about 1 minute to about 1 year, about 1 minute to about 48 hours, about 30 minutes to about 36 hours, about 5 minutes to 24 hours, or about 30 minutes to 2 hours. The contact time can be about 1 minute, 2 minutes, 5 minutes, 10 minutes, 30 minutes, 45 minutes, 1 hour, 1.5 hours, 2 hours, 2.5 hours, 3 hours, 5 hours, 10 hours, 20 hours, 24 hours, 36 hours, 48 hours, 5 days, 1 week, 20 weeks, 52 weeks, 1.5 years, 2 years, 2.5 years, 3 years, 3.5 years, 4 years, 4.5 years, or 5 years. In other embodiments, the contact time can be about 1 month to about 5 years, about 3 months to about 4 years, about 6 months to about 2 years.

As illustrated in FIG. 1, the biological tissue can be placed in the hydration media (FIG. 1, Step 1). In some embodiments, the biological tissue can be fully submerged in the hydration media (FIG. 1, Step 2). In other embodiments, the biological tissue can be partially submerged in the hydration media. When partially submerged, between about 1-99% of the surface area of the biological tissue can be submerged, between about 10-90% of the surface area of the biological tissue can be submerged, between about 20-80% of the surface area of the biological tissue can be submerged, between about 30-70% of the surface area of the biological tissue can be submerged, between about 40-60% of the surface area of the biological tissue can be submerged, or between about 45-55% of the surface area of the biological tissue can be submerged. In some embodiments, the biological tissue can be coated with the hydration media. When coated, between about 1-99% of the surface area of the biological tissue can be coated, between about 10-90% of the surface area of the biological tissue can be coated, between about 20-80% of the surface area of the biological tissue can be coated, between about 30-70% of the surface area of the biological tissue can be coated, between about 40-60% of the surface area of the biological tissue can be coated, or between about 45-55% of the surface area of the biological tissue can be coated. In other embodiments, the biological tissue can be stored in a closed container with a minimal amount of hydration media to maintain a humid environment of about 50% to about 100% relative humidity throughout the storage period. After contact with the hydration media, the biological tissue can be removed prior to use (FIG. 1, Step 3). In some embodiments, the biological tissue can be placed in contact with other biocompatible solutions (e.g., normal saline), prior to use. In other embodiments, excess hydration media can be removed from the biological tissue by draining, rinsing, squeezing, or other suitable drying method. In preferred embodiments, the biological tissue can be used as an implant into a patient.

In some embodiments, the hydration media can preserve the inherent physical properties within the biological tissues throughout the hydrated storage time period of about 1 minute to 5 years, about 1 minute to 3 years, about 1 minute to about 1 year, about 1 minute to about 48 hours, about 30 minutes to about 36 hours, about 5 minutes to 24 hours, or about 30 minutes to 2 hours. The contact time can be about 1 minute, 2 minutes, 5 minutes, 10 minutes, 30 minutes, 45 minutes, 1 hour, 1.5 hours, 2 hours, 2.5 hours, 3 hours, 5 hours, 10 hours, 20 hours, 24 hours, 36 hours, 48 hours, 5 days, 1 week, 20 weeks, 52 weeks, 1.5 years, 2 years, 2.5 years, 3 years, 3.5 years, 4 years, 4.5 years, or 5 years. In other embodiments, the contact time can be about 1 month to about 5 years, about 3 months to about 4 years, about 6 months to about 2 years. As used herein, physical properties can include a growth factor (including BMP-2, BMP-4, BMP-7, and IGF-1), elasticity, compressive strength, and shear strength. At least one physical property can be preserved. The physical properties can be preserved by between about 25% and 99%, between 30% and 90%, between 25% and 90%, between 40% and 80%, between 50% and 70%, or between 55% and 65% of the products initial properties. The products initial properties are defined immediately post manufacturing when the product is ready for sale. One skilled in the art would understand that the products initial properties does not need to be a measurement of an actual product's properties, but instead can be an average of the properties values for a given product from samples of the product. In some embodiments, at least one physical property can be between preserved compared to the products initial properties by about 25%, about 30%, about 35%, about 40%, about 45%, about 50%, about 55%, about 60%, about 65%, about 70%, about 75%, about 80%, about 85%, about 90%, about 95%, or about 99%.

In some embodiments, the hydration media can be used to fully hydrate a product. In these instances, the physical properties can be preserved to between about 25% and 99%, between 30% and 90%, between 25% and 90%, between 40% and 80%, between 50% and 70%, or between 55% and 65% as compared to the products properties immediately before dehydration.

The biological tissue can be fully hydrated, partially dehydrated, or fully dehydrated prior to placing in the hydration media. In some embodiments, fully dehydrated biological tissue can have less than about 10% residual moisture, less than about 6% residual moisture, or less than about 2% residual moisture. Methods of partially or fully dehydrating tissue are well known in the art and include the use of convectional aeration, vacuum desiccation, vacuum dehydration, and lyophilization. Tissues made from any of these methods can be rehydrated with the hydration media or stored in the hydration media.

In some embodiments, the biological tissue can be demineralized bone. The demineralized bone can have a residual calcium level of less than about 8%, less than about 6%, or less than about 2%.

The biological tissue can be shaped specifically to fill a void. The void can be determined by pre-assessment of a void, such as a bone void within a patient. The final use of the biological tissue can be implantation into a patient.

An aspect of the invention is a kit that includes a biological tissue and a hydration media in a container. The surface area of the interior of the container can be at least 1% greater than the surface area of the biological tissue. In some embodiments, the container can be sealed with the biological tissue and the hydration material. When the container is closed with the biological tissue and the hydration media inside, the humidity inside the container can be maintained between 20 and 100% relative humidity. The relative humidity can be between 30% and about 90%, about 40% and about 80%, about 50% and about 70%, about 60% and about 65%. In some embodiments, the relative humidity can be about 20%, about 22%, about 26%, about 32%, about 45%, about 48%, about 52%, about 55%, about 58%, about 62%, about 65%, about 68%, about 72%, about 75%, about 78%, about 82%, about 85%, about 92%, about 95%, about 97%, about 99%, or about 100%. The tissue can be stored for between about 30 minutes and about 5 years, about 1 hour and about 4 years, about 24 hours and about 3 years, or about 1 year and about 2 years. In some embodiments, the tissue can be stored for about 30 minutes, about 1 hours, about 4 hours, about 8 hours, about 16 hours, about 24 hours, about 36 hours, about 48 hours, about 56 hours, about 3 days, about 1 month, about 3 months, about 6 months, about 8 months, about 18 months, about 24 months, about 2.5 years, about 3 years, about 3.5 years, about 4 years, about 4.5 years, or about 5 years.

The container is preferably made of a material that is inert to the hydration material. Suitable materials include, but are not limited to, stainless steel, glass, foil, impermeable thermoplastic films, and combinations thereof. In some embodiments, where a lid is provided to seal the container, the lid can be made of polymeric materials, such as nylon, polypropylene, polystyrene or combinations thereof. Alternatively, the lid can be made of glass, or a metallic material.

EXAMPLE

Example 1. Production of Hydration Medium

Purified water (500 mL) was combined with sodium phosphate dibasic, anhydrous (11.50 grams), sodium phosphate monobasic, anhydrous (2.28 grams), and calcium silicate (58 mg). The solids were stirred at room temperature (approximately 72° C.) until dissolved. Purified water was added to a final volume of one liter to provide a final pH level of 7.4.

Ranges have been discussed and used within the forgoing description. One skilled in the art would understand that any sub-range within the stated range would be suitable, as would any number within the broad range, without deviating from the invention.

The foregoing description of the hydrated media invention, methods of making and methods of using the hydration media have been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

The invention claimed is:

1. A hydration medium for hydrating or storing bone, comprising:
 a solution comprising:
  a sodium phosphate;
  a calcium silicate; and water, wherein the osmolality of the hydration media is from about 200-about 400 milliosmoles per kilogram.

2. The hydration medium of claim 1, wherein the calcium silicate component is present at a concentration of about 0.025-about 0.100 milligrams per milliliter.

3. The hydration medium of claim 1, further comprising at least one of a potassium, a chloride, and a magnesium.

4. The hydration medium of claim 1, wherein a pH of the hydration media is between 7.0 and 7.7.

5. The hydration medium of claim 1, further comprising at least one additional solvent comprising an ethanol, a dimethylsulfoxide, or a glycerol.

6. The hydration medium of claim 1, wherein the bone is selected from the group comprising an allogeneic, an autogeneic, a xenogeneic, and combinations thereof.

7. The hydration medium of claim 1, wherein the bone is selected from the group consisting of a cortical bone, a cancellous bone, and combinations thereof.

8. The hydration medium of claim 1, wherein the bone is at least one of a fully demineralized bone, a partially demineralized bone, or a mineralized bone.

9. A method of using the hydration medium of claim 1, comprising:
placing the bone in the hydration media;
removing the bone from the hydration media; and
implanting the bone into a patient.

10. The method of claim 9, wherein the bone contacts the hydration media for between about two to about five years prior to the implantation.

11. The method of claim 9, wherein the bone contacts the hydration media for less than about 48 hours prior to the implantation.

12. The method of claim 9, wherein the bone contacts the hydration media to rehydrate the bone prior to the implantation.

13. The method of claim 9, wherein the hydration media prevents at least one mineral in the bone from leaching.

14. A method of making the hydration media of claim 1, comprising:
combining at least one sodium source and at least one calcium silicate in a water to form the hydration media, wherein an osmolality range of about 200 to about 400 milliosmoles per kilograms (mOsm/kg), wherein the calcium silicate is present in the hydration media at a concentration of about 0.010 to about 0.150 milligrams per milliliter.

15. The method of claim 14, further comprising adding between about 5 to about 50 osmolar (total) of at least one solute to the hydration media.

16. The method of claim 14, further comprising adjusting a pH of the hydration media to between about 5.0 to about 10.0 by adding an aqueous solution of acid or base as needed, ensuring the osmolality range remains about 200 to about 400 milliosmoles per kilogram.

17. The method of claim 14, further comprising adding between at least 1 vol. % and about 25 vol. % of a solvent to the hydration media.

18. The method of claim 14, further comprising mixing the sodium source and the calcium silicate at a temperature between 15° C. and about 50° C., and wherein the sodium source is at least one of a sodium phosphate dibasic, a sodium phosphate monobasic, and wherein the sodium source is anhydrous or hydrated.

* * * * *